US005493064A

United States Patent [19]

Vanderspurt et al.

[11] Patent Number: 5,493,064
[45] Date of Patent: Feb. 20, 1996

[54] NOBLE METAL LARGE PORE ZEOLYTE CATALYST FOR METHANOL-ETHANOL COUPLING

[75] Inventors: Thomas H. Vanderspurt, Delaware Township, N.J.; Jar-Lin Kao, Houston, Tex.

[73] Assignee: Exxon Research and Engineering Company, Florham Park, N.J.

[21] Appl. No.: 354,984

[22] Filed: Dec. 13, 1994

[51] Int. Cl.$^6$ .......................... C07C 29/34; C07C 31/10; C07C 31/12
[52] U.S. Cl. ............................... 568/905; 568/902.2
[58] Field of Search .................... 568/902, 902.2, 568/905

[56] References Cited

U.S. PATENT DOCUMENTS

| | | | |
|---|---|---|---|
| 3,972,952 | 8/1976 | Clark | 568/905 |
| 3,979,466 | 9/1976 | Yates | 568/905 |
| 4,400,561 | 8/1983 | Mitchell et al. | 568/902.2 |
| 4,568,656 | 2/1986 | Poppelmeier et al. | |
| 4,954,665 | 9/1990 | Vidal | 568/902.2 |
| 5,095,156 | 3/1992 | Radlowski et al. | 568/902.2 |
| 5,300,695 | 4/1994 | Radlowski | 568/905 |
| 5,348,924 | 9/1994 | Potter et al. | |

FOREIGN PATENT DOCUMENTS 219354  4/1887  European Pat. Off. .

OTHER PUBLICATIONS

Breck, *Zeolite Molecular Sieves* Krieger & Co., Malabar Fl (1984) pp. 49, 156, 163, 177, 361, 363, 369.

*Primary Examiner*—Joseph E. Evans
*Attorney, Agent, or Firm*—Linda M. Scuorzo

[57] ABSTRACT

The present invention discloses an alcohol coupling process in which a vaporized mixture of starting alcohols, preferably methanol and ethanol, is reacted with syngas in the presence of a large pore L zeolite, Y zeolite or large port mordenite, to form at least one alcohol coupling product having a greater number of carbon atoms than all of the starting alcohols. The large pore zeolite preferably has a substantial absence of strongly acidic catalytic sites and the reaction preferably produces the product alcohol in the substantial absence of $C_{6+}$ oxygenates.

2 Claims, No Drawings

NOBLE METAL LARGE PORE ZEOLYTE CATALYST FOR METHANOL-ETHANOL COUPLING

FIELD OF THE INVENTION

The present invention relates to a method for converting mixtures of methanol and ethanol in the presence of syngas to primarily n-propanol and isobutanol.

BACKGROUND OF THE INVENTION

Environmental concerns about motor vehicle exhaust pollution have increased the demand for compounds like methyl tertiary butyl ether, ethyl tertiary butyl ether and methyl tertiary amyl ether as reformulated gasoline components. The production of these oxygenates requires besides methanol and ethanol isobutylene for the tertiary butyl ethers or either 2-methyl-butene or 2-methyl-2-butene (β-isoamylene). Additionally, the continuing discovery of large amounts of natural gas relative to liquid petroleum have increased the need for processes to convert natural gas to high value, easily transportable liquids. There is well known technology to convert natural gas into methanol and emerging technology to convert natural gas into methanol, ethanol mixtures. These lower alcohols have significantly lower energy density than gasoline and present both corrosion and compatibility problems in the presence of moisture. Thus, there is a need for catalysts than can convert simple alcohols such as methanol and ethanol into higher alcohols such as n-propanol and isobutanol. Isobutanol can be readily converted to isobutylene and thence to methyl tertiary butyl ether. Catalysts that produce isobutanol along with methyl butanols that can be readily dehydrated to either 2-methyl-butene or 2-methyl-2-butene (β-isoamylene) are also desirable. However, the co-production of significant amounts of six carbon and higher alcohols and other oxygenates is not desirable for the production of high octane, gasoline compatible oxygenates.

SUMMARY OF THE INVENTION

The present invention provides for an alcohol coupling process, comprising contacting a vaporized mixture of starting alcohols of methanol in combination with a second alcohol selected from the group consisting of ethanol, n-propanol, and mixtures thereof with a carrier gas containing syngas, in the presence of a large pore zeolite to form at least one alcohol (i.e. coupling product) having a higher molecular weight and greater number of carbon atoms than the starting alcohols.

Preferably in the present invention the zeolite is selected from the group consisting of noble metal loaded alkali treated containing L, Y zeolites and large port mordenite. The contacting is preferably carried out at a temperature of from about 300° C. to about 400° C., under a pressure of from about 2,000 kPa to about 15,000 kPa and at a space velocity of from about 4,000 $hr^{-1}$ to about 10,000 $hr^{-1}$. Preferably the product alcohols are produced in the substantial absence of $C_{6+}$ oxygenates.

The invention may suitably comprise, consist or consist essentially of the elements or steps disclosed herein.

DETAILED DESCRIPTION OF THE INVENTION

Catalysts are known that can convert synthesis gas directly to mixtures of methanol, ethanol, n-propanol, isobutanol and 2-methyl butanol. However these catalysts also produce unwanted higher molecular weight compounds along with varying amounts of methane and light, low value gaseous alkanes. It is desirable to produce n-propanol and isobutanol in the substantial absence of such materials.

The present invention provides a process for using a heterogeneous noble metal/large pore zeolite catalysts to convert mixtures or streams containing the lower value alcohols, methanol and ethanol, in the presence of syngas (mixtures of hydrogen and gaseous carbon oxides, including CO and $CO_2$ and equivalents to the foregoing mixtures of hydrogen gas and gaseous carbon oxides, e.g., CO and steam) to preferentially mixtures containing primarily higher alcohols, desirably high octane, gasoline-compatible alcohols, n-propanol and isobutanol, i.e., in the substantial absence of gaseous alkanes (e.g., methane and other light low value gaseous alkanes) and $C_6$ and higher (i.e., $C_{6+}$) oxygenates. The higher alcohols are presently in greater demand commercially as commodity chemicals. In addition to the advantage of producing the aforementioned desirable oxygenates the process of the present invention minimizes certain undesirable side reactions, such that the desirable oxygenated products may be produced in the substantial absence of $C_{6+}$ oxygenates, such as 2-methyl pentanol. Thus the present invention produces relatively less higher molecular weight by products than do non-zeolitic, supported noble metal catalysts. The process also minimizes the decomposition of methanol to the decomposition products of carbon monoxide and hydrogen. Advantageously, the catalyst also remains stable in the presence of CO in the process.

The starting materials described herein may be obtained commercially or made by known methods.

Accordingly, it has been discovered that mixtures of methanol and ethanol vapor in the presence of synthesis gas are conveniently converted to mixtures of higher alcohols, particularly n-propanol and isobutanol by passage over a noble metal loaded/large pore zeolite catalyst. For best results the methanol should be in excess to other alcohols. Optionally a portion of the n-propanol may be recycled to increase the overall production of isobutanol. The synthesis gas (syngas), contains hydrogen and carbon monoxide and optionally may also contain water, carbon dioxide and light hydrocarbons such as methane, as well as inert gases such as nitrogen, argon and mixtures thereof. The partial pressures of hydrogen and carbon monoxide used should be close to that required for stability of the methanol due to the thermodynamic equilibrium at elevated temperatures between hydrogen, carbon monoxide and methanol. The zeolite used should be highly crystalline desirably with a substantial absence of detrital material in the pores and have free apertures of at least about 6 A. Examples of such materials include Zeolite Y, Large Port Mordenite (Zeolon) and Zeolite L, a further description of which may be found in Breck, *Zeolite Molecular Sieves*, R. E. Krieger Publishing Co., Malabar, Fla. (1984) pp. 49, 156, 163, 177, 361, 363, 369. For use in commercial reactors it is usually advisable to form the zeolite based catalyst into aggregates such as tablets, spheres, extrudates or the like. If catalyst powder is used the powders are typically compressed between about 90–1800 $kg/cm^2$, more typically 450–900 $kg/cm^2$. This may be accomplished by mixing an inorganic material such as clay, silica or alumina with the zeolite crystals in a manner to bind the mass together as an aggregate. Such an aggregate should have sufficient mechanical strength to withstand handing and use and the binder should not interfere with the catalytic properties of the finished catalyst nor with its regenerability. U.S. Pat. No. 5,348,924 for example, describes techniques for extruding zeolites, especially L zeolite using an alumina binder, and is incorporated herein by reference.

For the catalytic reaction of coupling methanol with ethanol to form n-propanol and of coupling methanol with n-propanol to form isobutanol to occur there should be a sufficiency of catalyst active sites that are desirably amphoteric or basic in nature. It is likewise important that the catalyst have a substantial, preferably an essential absence, of strongly acidic sites, i.e. sites favoring or selective to the production of dimethyl ether and other less desirable products. Similarly since it is presently hypothesized that this coupling requires a dehydrogenated species similar to an aldehyde reacting in conjunction with the active site it is desirable to have a metal with hydrogenation and dehydrogenation activity. This metal however must have a reduced or essential absence of Fischer-Tropsch catalytic activity, and methanation activity. Thus of the Group VIII catalytically active metals, Pt and Pd are preferred and Pd is most preferred. The amount of metal may vary from 0.1% to 2% or more, although larger amounts usually are not usually cost effective. U.S. Pat. No. 4,568,656 teaches a method for the ion exchange loading of zeolitic catalysts such as L with noble metals. If the ion exchange method is used sufficient alkali metal cation concentration and valence must be retained by the catalyst prior to drying such that after reduction (i.e. in presence of syngas) of the noble metal ions to the metal there are sufficient alkali metal cations available to be effective to neutralize acid sites formed. When an incipient wetness method is used the alkali metal cations originally present in the zeolite are retained.

The catalyst should be in a form suitable for the reactor, and it is advisable to flush the reactor with an inert gas, typically nitrogen or argon prior to introducing the reducing gas to insure the noble metal component is converted to the highly dispersed metallic state. The presence of a highly dispersed metal component as described above is essential. A number of methods known in the art may be used to ensure such a reduction of the metal component precursor or precursors to the highly dispersed state. One such method is described below. The temperature should be increased to dry the catalyst charge and to reduce the noble metal under mild conditions to produce a highly dispersed noble metal, typically up to about 100° C. under as high a flow rate of inert gas, and at as low a pressure as is practical for the particular reactor configuration, as is well known to those skilled in the art. The bed typically may be prepared by holding the temperature for 1 minute per cm of bed depth at a flow rate of about 60 sccm per cm$^3$ of bed volume or higher at as low a pressure as practicable, and introducing hydrogen into the inert gas, and increase the temperature at a rate not exceeding 8° C./minute. The hydrogen introduction should be such that the partial pressure of hydrogen over the catalyst does not exceed about 70 kPa when the temperature reaches about 200° C. At about 200° C. the temperature is held for 1 minute per cm of bed depth at a flow rate of about 60 sccm per cm$^3$ of bed volume. Then the temperature is raised typically at a rate not exceeding 4° C./minute to about 260° C. and held for about 1 minute per cm of bed depth, and hydrogen flow rate is increased to about 200 sccm per cm$^3$ of bed volume and the hydrogen partial pressure is increased to about 100 kPa. Once these conditions are achieved they are held for about 2 minutes per cm of bed depth. The temperature is then increased typically up to a 3° C./minute to about 400° C. and held for about 1 hour, at which point the reactor is typically adjusted to operating temperature and the pressure increased to operating pressure as the gas in the reactor is changed to the desired syngas composition. At reaction startup conditions, the hydrogen to carbon monoxide ratio may be between 3:1 to 0.3:1 with the range 1.5:1 to 0.4:1 preferred and 1.0 to 0.5:1 most preferred. The syngas pressure is a function of the $H_2$:CO ratio and the methanol flow rate, that is, the methanol partial pressure at the inlet of the bed. Desirable conditions are such that the partial pressure of methanol predicted by thermodynamic calculations is between about 90 and 110% of that predicted by the partial pressures of hydrogen and carbon monoxide at the bed inlet and the average bed temperature. Lower syngas partial pressure will result in the loss of methanol to gas while higher partial pressure will result in the production of some methanol. Excessive hydrogen partial pressures will slow the rate of alcohol coupling while increasing the preferential production of undesirable light alkanes. As is well known to those skilled in the art the metallurgy of the reactor interior and all transfer lines must be such as to retard or prevent the formation of metal carbonyls which will result in the formation of either a methanation of Fischer-Tropsch type catalyst and the production of increasing amounts of unwanted hydrocarbons and other materials.

Once the catalyst is under syngas at the desired conditions the mixture of lower alcohols reactants is introduced. The number of carbon atoms in the lower alcohol starting material is limited by its ability to be vaporized and passed over the catalyst at a temperature that avoids substantial decomposition of the catalyst, the starting materials or the resulting higher alcohol end products. Preferred are methanol and ethanol the amount of ethanol used should be on a molar basis between 5 and 25% of the amount of methanol used. Higher levels of ethanol will result in increased levels of n-butanol byproduct while lower levels result in the inefficient use of the system. If the product n-propanol is to be fed with, or recycled into the reactant stream, the molar amount of ethanol and n-propanol should be between 5 and 25% of the amount of methanol with about 8 to 16% preferred. Insufficient methanol can lead to increased undesirable by-product production. The operating temperature may be between about 300° C. and 400° C. or higher, but as described earlier the pressure, temperature, syngas ratio and methanol feed rate are all related by methanol decomposition thermodynamics. The amount of catalyst employed and the rate at which the reactant gas mixture is contacted therewith should be adequate to result in a residence time that is sufficient to enable the catalyst to convert the starting materials to the desired alcohol products. Generally, this may be accomplished by adjusting the amount of catalyst and rate of contact to give a space velocity of from about 4,000 to about 10,000 hr$^{-1}$. As mentioned previously the syngas may also contain water, carbon dioxide and light hydrocarbons such as methane as well as inert gases. However, it is extremely desirable however to purify the gases before use to thoroughly remove impurities that are known to act as poisons to the catalyst or the reaction, such as sulfur or sulfur containing compounds such as, hydrogen sulfide, carbonyl sulfide, mercaptans and thiols.

In general after the feed is passed over the catalyst it will produce a mixture having at least one alcohol having a higher molecular weight and greater number of carbon atoms than any of the starting alcohol or alcohols. Thus, for example, a mixture of methanol and ethanol produces at least isobutanol.

EXAMPLES

Example 1

A sample of KL zeolite was prepared according to European Patent Specification 0 219 354 B1, and was converted to an alumina bound 1/16" diameter extrudate according to U.S. Pat. No. 5,348,924, incorporated herein by reference and loaded with palladium by the following incipient wetness method: A Pd stock solution was prepared by dissolving 0.6021 g of $Pd(NH_3)(NO_3)_2 \cdot H_2O$)(Pd assay 35.64%) in 19.4129 g water. Into 24.98 g of dry 1/16" KL extrudate (vacuum dried a +150° C. for 4 hours) there was added a Pd loading solution containing 10.7272 g of the above Pd stock solution and 9.2085 g of water. After shaking for 2 minutes the mixture was allowed to stand at ambient temperature ($\simeq$23° C.) for 1 hour. The wet extrudate was dried at 120° C. for 4 hours and calcined at 486° C. for 3 hours then reduced in flowing hydrogen at 520° C. for 1 hour. The Pd content was 0.46 wt %. The extrudate was crushed and sieved to give 4.8 cm$^3$ of 60 to 80 mesh (approximate diameters from 180 μm to 250 μm) granules with a mass of 3.0677 grams. This was mixed with 6 cm$^3$, 7.6907 grams of high purity, 40 to 60 mesh (250 μM to 425 μm approximate diameter), crushed, fused quartz. This was charged to a copper jacketed, copper lined stainless steel reactor tube with an interior diameter of about 0.9525 cm equipped with a copper sheathed, axial thermowell about 0.3175 cm in outside diameter.

After installation of the reactor tube in a vertical furnace and connection to feed and product collection systems the reactor tube was thoroughly flushed with argon. Then the catalyst was heated from room temperature to 100° C. at 8° C. per minute during which time the gas composition was changed from 100% argon to of 34% argon and 66% hydrogen at about 1 atmosphere pressure flowing at about 300 sccm. The temperature was then increased at 8° C. per minute to 200° C. then at 4° C./min to 260° C. It was held there for 1 minute and then the atmosphere was gradually changed to about 100% hydrogen flowing at 1000 sccm. Under hydrogen it was then held at 260° C. for 5 minutes before the temperature was increased to 400° C. at 3° C./min. where it was held for 1 hour. It was then cooled at 2° C./minute to 380° C. and the gas composition changed to about 44.12% CO, 39.33% $H_2$, 9.98% Ar (Internal standard) and 6.57% $CO_2$. This was passed over the catalyst at a rate of 399 SCCM and a total pressure of 6591 kPa.

Example 2

A solution containing: 27.693 g $Mn(NO_3)_2 \cdot 6 H_2O$, 17.938 g $Zn(NO_3)_2 \cdot 6H_2O$ and 21.554 g $ZrO(NO_3)_2 \cdot xH_2O$ in 500 mls of distilled water was prepared. A second solution then calcined in air with the oven temperature increased smoothly from room temperature 425° C., from 13.02 g of material was recovered.

A Pd solution containing 81.4 mg $Pd(NO_3)_2 \cdot xH_2O$ and 15 drops of ethanolamine in 10 mls of distilled water was prepared. This was slurried with the cooled $Mn_{1.8}Zn_{1.17}ZrO_{8.2}$ solid. The slurry was then dried for 1.5 hours at $\simeq$100° C. in a vacuum oven. Then it was calcined in air with the oven temperature smoothly increased from room temperature to 325° C. over the course of 1 hour and held at 325° C. for 3 hours before cooling to room temperature over the course of an hour. Subsequent analysis revealed a Pd concentration of 0.23 wt % and a surface area of 200 M$^2$/g. The Li concentration in this catalyst was by analysis <0.3 ppm.

The calcined catalyst was crushed and sieved to give 3.0 cm$^3$ of 60 to 80 mesh (approximate diameters from 180 μm to 250 μm) granules with a mass of 2.9775 grams. This was mixed with 6 cm$^3$, 7.6768 grams of high purity, 40 to 60 mesh (250 μM to 425 μm approximate diameter), crushed, fused quartz. This was charged to a copper jacketed, copper lined stainless steel reactor tube with an interior diameter of about 0.9525 cm equipped with a copper sheathed, axial thermowell about 0.3175 cm in outside diameter.

After installation of the reactor tube in a vertical furnace and connection to feed and product collection systems the reactor tube were thoroughly flushed with argon. Then the catalyst was heated from room temperature to 100° C. at 8° C. per minute during which time the gas composition was changed from 100% argon to of 34% argon and 66% hydrogen at about 1 atmosphere pressure flowing at about 300 sccm. The temperature was then increased at 8° C. per minute to 200° C. then at 4° C./min. to 260° C. It was held there for 1 minute and then the atmosphere was gradually changed to about 100% hydrogen flowing at 1000 sccm. Under hydrogen it was then held at 260° C. for 5 minutes before the temperature was increased to 400° C. at 3° C./min. where it was held for 1 hour. It was then cooled at 2° C./min. to 380° C. and the gas composition changed to about 44.00% CO, 39.39% $H_2$, 10.01% Ar (Internal standard) and 6.59% $CO_2$. This was passed over the catalyst at a rate of 399 SCCM and a total pressure of about 6500 kPa.

Table 1 describes the results of Example 1 and Example 2.

TABLE 1

| Cat Eg# | T° C. | H$^2$/CO | Atm H$_2$ + CO | GHSV | % EtOH Conv. | C% iBuOH | C% nPrOH | C% HC gas | C% MBuOH | C% C6+ | C% C5+ |
| --- | --- | --- | --- | --- | --- | --- | --- | --- | --- | --- | --- |
| 1 | 383.0 | 0.9 | 54.2 | 5270 | 72.8 | 45.01 | 37.36 | 3.21 | 5.82 | 6.09 | 11.92 |
| 1 | 362.8 | 0.9 | 54.2 | 5270 | 47.1 | 45.78 | 35.38 | 3.69 | 4.15 | 8.58 | 12.73 |
| 1 | 342.7 | 0.9 | 54.2 | 5270 | 34.7 | 44.86 | 36.00 | 3.33 | 3.08 | 9.61 | 12.69 |
| 2 | 351.0 | 0.9 | 56.0 | 8450 | 96.5 | 60.69 | 7.44 | 7.70 | 8.37 | 15.33 | 23.70 |
| 2 | 336.2 | 0.9 | 56.0 | 8450 | 79.1 | 44.61 | 20.33 | 11.80 | 9.33 | 11.65 | 20.98 | containing 21.0 g LiOH in 500 mls of distilled water was prepared. These two solutions were added with rapid stirring to 600 mls of distilled water maintained at 70° C. in such a manner as the pH of the resulting slurry was maintained at 9.0. After the addition was complete the slurry was stirred at 70° C. for an additional 5 hours then allowed to cool to room temperature. The light brown precipitate was recovered by filtration and then washed three times with 1000 ml portions of distilled water. The pH of the final filtrate was 7.8. The washed precipitate was dried overnight at 130° C. It was

What is claimed is:

1. An alcohol coupling process, comprising:

contacting a vaporized mixture of starting alcohols of methanol in combination with a second alcohol selected from the group consisting of ethanol, n-propanol, and mixtures thereof with a carrier gas containing CO and $H_2$ in the presence of an alumina-bound highly dispersed metallic Pd-loaded, alkali metal cation exchanged L zeolite wherein the zeolite and alumina have an essential absence of strongly acidic catalytic sites and wherein said contacting is carried out at a temperature and partial pressure of CO and H of from about 300° C. to 400° C. and from 2000 kPa to about 15,000 kPa, at a sufficient pressure to minimize the decomposition of methanol to CO and $H_2$ and at a space velocity of from about 4000 $hr^{-1}$ to about 10,000 $hr^{-1}$ to produce isobutanol and n-propanol in the substantial absence of light gaseous alkanes and $C_{6+}$ oxygenates.

2. The process of claim 1 wherein the alkali is potassium.

* * * * *